(12) United States Patent
Brochard et al.

(10) Patent No.: US 9,713,689 B2
(45) Date of Patent: Jul. 25, 2017

(54) METHODS OF EVALUATING A PATIENT FOR PEEP THERAPY

(76) Inventors: Laurent Brochard, Creteil (FR); Alain Mercat, Anders (FR); Jean-Christophe M. Richard, Rouen (FR); Jean Dellamonica, Nice (FR)

(*) Notice: Subject to any disclaimer, the term of this patent is extended or adjusted under 35 U.S.C. 154(b) by 873 days.

(21) Appl. No.: 12/834,354

(22) Filed: Jul. 12, 2010

(65) Prior Publication Data

US 2012/0010520 A1    Jan. 12, 2012

(51) Int. Cl.
*A61B 5/087* (2006.01)
*A61M 16/00* (2006.01)
*A61B 5/091* (2006.01)

(52) U.S. Cl.
CPC ......... *A61M 16/0051* (2013.01); *A61B 5/091* (2013.01)

(58) Field of Classification Search
CPC .. A61M 16/00; A61M 2230/005; A61B 5/091
See application file for complete search history.

(56) References Cited

U.S. PATENT DOCUMENTS

| | | | |
|---|---|---|---|
| 5,088,332 A | 2/1992 | Merilainen et al. | |
| 5,540,233 A | 7/1996 | Larsson et al. | |
| 5,915,381 A | 6/1999 | Nord | |
| 5,961,447 A * | 10/1999 | Raviv et al. | 600/300 |
| 6,139,506 A | 10/2000 | Heinonen | |
| 6,315,739 B1 | 11/2001 | Merilainen et al. | |
| 2007/0062533 A1 | 3/2007 | Choncholas et al. | |
| 2008/0185009 A1 | 8/2008 | Choncholas et al. | |
| 2011/0197886 A1* | 8/2011 | Guttmann et al. | 128/204.23 |

OTHER PUBLICATIONS

Effect of CPAP on intrinsic PEEP, inspiratory effort, and lung volume in severe stable COPD F O'Donoghue, P Catcheside, A Jordan, A Bersten, R McEvoy Thorax. Jun. 2002; 57(6): 533-539. doi: 10.1136/thorax.57.6.533.*
Prone position improves expiratory airway mechanics in severe chronic bronchitis. Mentzelopoulos SD, Roussos C, Zakynthinos SG. Eur Respir J. Feb. 2005;25(2):259-68.*
U.S. Appl. No. 11/549,754, filed Oct. 16, 2006.

* cited by examiner

*Primary Examiner* — Patricia Mallari
*Assistant Examiner* — Michael Catina
(74) *Attorney, Agent, or Firm* — Andrus Intellectual Property Law, LLP

(57) ABSTRACT

Methods of automatically evaluating a patient for positive and expiratory pressure (PEEP) therapy include providing respiratory assistance to the patient with a mechanical ventilator. The patient is provided PEEP therapy at a first PEEP. A first end expiratory lung volume (EELV) is measured from the patient. PEEP therapy is provided to the patient at a second PEEP. A second EELV is measured from the patient. A difference from the first EELV and the second EELV is calculated. A value indicative of the patient's response to PEEP therapy is calculated from the difference between the first EELV and the second EELV.

16 Claims, 5 Drawing Sheets

METHODS OF EVALUATING A PATIENT FOR PEEP THERAPY

BACKGROUND

The present disclosure relates to the fields of mechanical ventilation and respiratory support. More specifically, the present disclosure relates to a method of evaluating a patient for positive end expiratory pressure (PEEP) therapy.

Mechanical ventilation is a commonly accepted medical practice in the treatment of individuals experiencing respiratory problems. The patient may be too weak from disease and/or sedation from an anesthetic agent to complete an entire respiratory cycle under his own power. In these instances, mechanical ventilatory assistance is provided whereby patient's spontaneous breath attempts are detected by the ventilator and respiratory assistance is provided accordingly.

One specific form of respiratory therapy is the application of a positive and expiratory pressure (PEEP). During mechanical ventilation with (or without) PEEP, the patient is allowed to exhale naturally. The patient's natural exhalation is a function of the compliance and resistance of the patient's lungs. When an inspiratory pressure from the mechanical ventilator is terminated, the lungs return to a natural equilibrium state, forcing inspired air out of the lungs. PEEP therapy applies an external pressure to the lungs to maintain an elevated airway pressure reaching a new equilibrium state at a higher lung volume than without PEEP.

As a patient exhales, the pressure in the lungs drops until it approaches airway pressure. As the pressure within the lungs drops, the alveoli, or air sacs, in the lungs deflate. If alveolar sacs collapse completely, more pressure is required upon inspiration to reach the opening pressure and re-inflate the alveolar sacs. By applying PEEP, the additional pressure in the patient's lungs keeps more of these alveolar sacs from completely collapsing upon expiration and, as such, allows them to participate in ventilation. This decreases the relative pressure change required to re-inflate the lung and further increases the end expiratory lung volume (EELV) of the patient.

There are two components to the increased EELV as PEEP is increased. One component is due to the stretching of the lung by the increased pressure. A second, more desirable component, occurs from "recruiting" alveolar sacs by preventing their collapse upon exhalation, as described above.

The EELV component due to stretching, or distension, of the lungs is associated with a variety of risks to the patient. Excessive lung distension can cause compression of the pulmonary bed of the lung, loading on the right side of the heart, reducing blood volume available for gas exchange, as well as volutrautomatic damage to the lungs themselves.

BRIEF DISCLOSURE

The present disclosure relates to methods of evaluating a patient for PEEP therapy.

In one embodiment, a mechanical ventilator provides respiratory assistance to the patient. The mechanical ventilator provides PEEP therapy at a first PEEP. A sensor measures a first EELV of the patient at the first PEEP. The mechanical ventilator provides PEEP therapy to the patient at a second PEEP. The sensor measures a second EELV of the patient at the second PEEP. A processor calculates the difference between the first EELV and the second EELV. The processor further calculates a value indicative of the patient's response to PEEP therapy.

A non-transient computer readable medium comprises computer readable code that is executed by a processor. Upon execution of the computer readable code, the processor obtains a first lung volume at a first PEEP. The processor further obtains a second lung volume at a second PEEP. The processor calculates a change in lung volume between the first lung volume and the second lung volume. The processor calculates a recruitment index by dividing the change in lung volume by the first lung volume. The processor evaluates the patient for PEEP therapy based upon the recruitment index.

In a further embodiment of a method of automatedly evaluating a patient for PEEP therapy, PEEP therapy is provided to a patient at a first PEEP with a mechanical ventilator. A sensor measures a first EELV of the patient at the first PEEP. The mechanical ventilator provides PEEP therapy to the patient at a second PEEP. The volumetric sensor measures a second EELV of the patient at the second PEEP. A processor calculates a change in volume between the first EELV and the second EELV. The processor further calculates a recruitment index at a recruitment index as the ratio of the change in volume to the second EELV. The processor further evaluates the patient for PEEP therapy based upon the recruitment index.

DETAILED DISCLOSURE

Figure 1:
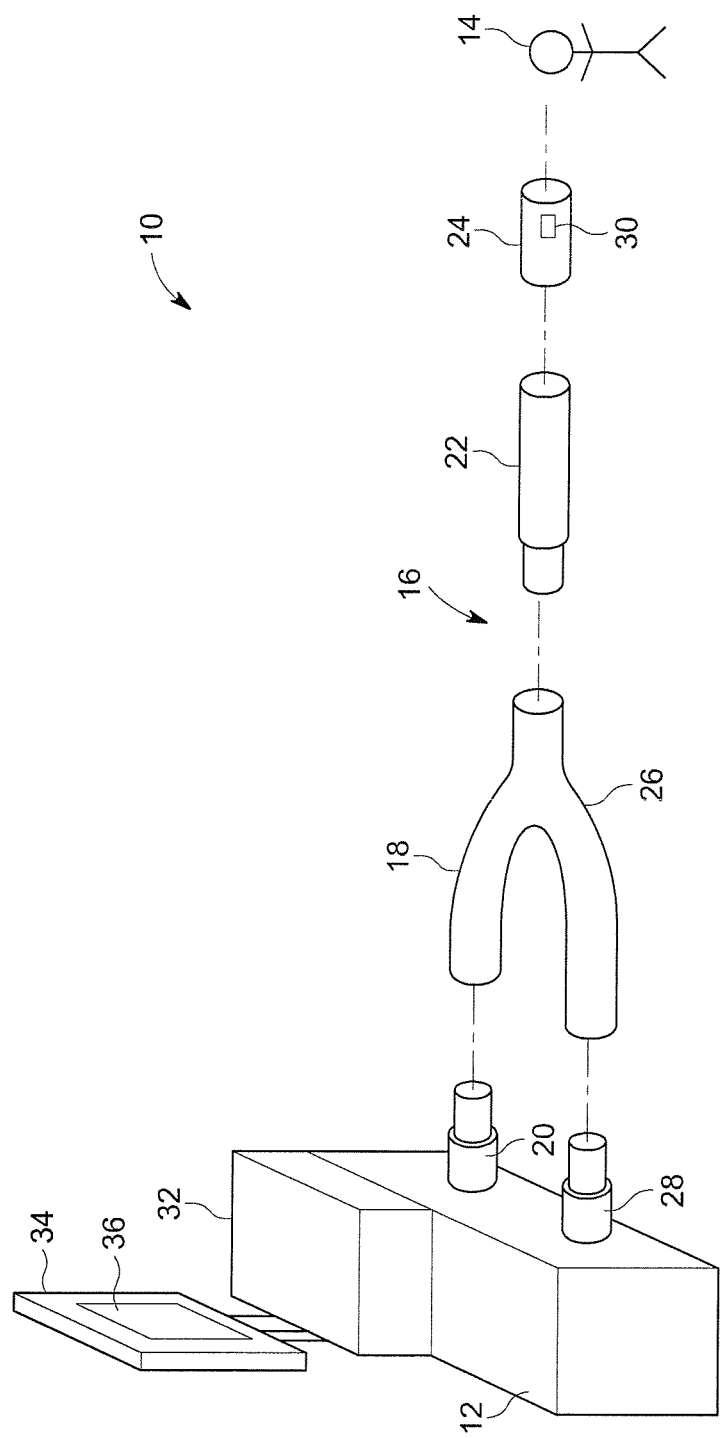
FIG. 1 is an environmental view of a ventilator system.

FIG. 1 depicts an environmental view of a ventilator system 10. The ventilator system 10 includes a mechanical ventilator 12 that operates to provide respiratory support or respiratory assistance to a patient 14. The mechanical ventilator 12 provides a flow of medical gas, which may include one or more of air, oxygen, nitrogen, and helium, and additionally may include additives such as aerosol drugs or anesthetic agents. The mechanical ventilator 12 provides the flow of medical gas to a breathing circuit 16 through an inspiratory limb 18 connected to an inspiratory port 20 of the mechanical ventilator 12. The medical gas travels through the inspiratory limb 18 into the patient limb 22 of the breathing circuit 16. The medical gas is delivered to the patient 14 through a patient connection 24.

Expired gases from the patient 14 are delivered back to the mechanical ventilator 12 through the patient connection 24 and the patient limb 22. The expired gases are directed into an expiratory limb 26 of the breathing circuit 16. The expired gases are returned to the mechanical ventilator 12 through an expiratory port 28.

The expiratory port 28 includes a controllable flow valve (not depicted) that is adjustable to regulate the pressure within the breathing circuit 16. Adjustment of this flow valve creates a back pressure applied to the patient 14 during exhalation causing a positive end expiratory pressure (PEEP). It is to be understood that this is one example of a system that can provide PEEP therapy to a patient 14, other systems and configurations as recognized by one of ordinary skill in the art are considered to be within the scope of the present disclosure.

The ventilator system 10 may further include a plurality of check valves (not depicted) which may be placed at various points along the breathing circuit 16 such as to only permit medical gas flow in a desired direction along the appropriate pathway towards or away from the patient 14.

Disposed within the patient connection 24, or alternatively, fluidly connected to another component of the breathing circuit 16, is a gas monitoring sensor 30. The gas monitoring sensor 30 may include one or more of pressure, flow, and gas concentration sensors that may be used by the mechanical ventilator 12 to monitor and control the operation thereof and provide feedback to a clinician. Exemplary embodiments of the gas monitoring sensor 30 that may be used are the D-lite MGas module and NCOVX gas module available from GE Healthcare.

The mechanical ventilator 12 further includes a central processing unit 32 which may include a microcontroller or processor. The CPU 32 executes computer readable code stored on a non-transient computer readable medium such as to operate the mechanical ventilator 12 and to provide feedback and control options to a clinician on a graphical display 34. The CPU 32 may control the graphical display 34 to present the feedback and control information on a graphical user interface (GUI) 36 presented on the graphical display 34. It will be understood by one of ordinary skill that alternative configurations for mechanical ventilator output and control may be used and are considered to be within the scope of this disclosure.

As noted above, one type of respiratory therapy that can be provided to a patient 14 by a mechanical ventilator 12 is the application of PEEP. PEEP increases a base line pressure within the patient's respiratory system such that natural exhalation by the patient maintains a higher airway pressure than respiration without PEEP therapy. Typical PEEP pressures range up to 20 cm $H_2O$, although higher PEEP pressures may also be used. High PEEP refers to PEEP therapy applied above 10 cm $H_2O$, and more specifically, 15-20 cm $H_2O$. Low PEEP refers to PEEP pressures below 10 cm $H_2O$ and which are often applied at 5-8 cm $H_2O$.

As noted above, the effects of PEEP therapy are measured in the patient by measuring the volume of the patient's lungs in response to the PEEP therapy. This is measured as the end expiratory lung volume (EELV) and is measured for a particular PEEP pressure applied to the patient. A special case of EELV is measured at zero PEEP (ZEEP). This measurement of EELV is referred to as functional residual capacity (FRC) and is a measurement of the volume of air that remains in the lungs at the end of natural expiration.

Increases in EELV associated with the application of PEEP come from two physiological sources. The first type of volume increase comes from the application of additional pressure on the lung tissue. This causes the lungs to distend, creating more lung volume. This presents risks to the patient in the form of volutrauma which damages the lungs. Volutrauma can result in medical complications with the patient similar to Acute Respiratory Distress Syndrome (ARDS). The second physiological cause of increased lung volume is the "recruitment" of alveoli. Alveoli are the air sacs within the lungs that promote gas exchange with the patient's blood. Some alveoli, particularly diseased or distressed alveoli, collapse when the pressure in the lungs falls too low.

PEEP therapy maintains a minimum airway pressure within the lungs causing these alveoli to remain open. This promotes gas exchange within the lungs as it requires more respiratory force to ventilate collapsed alveoli than to ventilate alveoli that are already open. Increased respiratory force causes greater shear stresses on the alveoli, which may result in further damaging the diseased or distressed alveoli. The recruitment of alveoli therefore also increases EELV.

When analyzing the effectiveness of PEEP therapy, it can be seen from the information above that it is desirable to promote increases in EELV based upon recruitment, while minimizing increases in EELV due to distention.

Currently, alveolar recruitment is only measured indirectly, such as by monitoring blood oxygenation (SpO2). It is assumed that increases in blood oxygenation are as a result of improved gas exchange in the lungs, which is provided by increased alveolar recruitment. The embodiments of methods disclosed in greater detail herein serve to quantify a portion of the change in EELV that is attributable to alveolar recruitment, such that it can be distinguished from changes in EELV that are attributable to lung distention. By analysis of these characterizations, a patient can be evaluated as a good candidate for PEEP therapy or a poor candidate for PEEP therapy. A good candidate for PEEP therapy is generally defined as a patient that will experience a substantial change in EELV due to recruitment rather than distention, while a patient that is a poor candidate for PEEP therapy is one that will have more change in EELV due to distention rather than recruitment.

Figure 2:
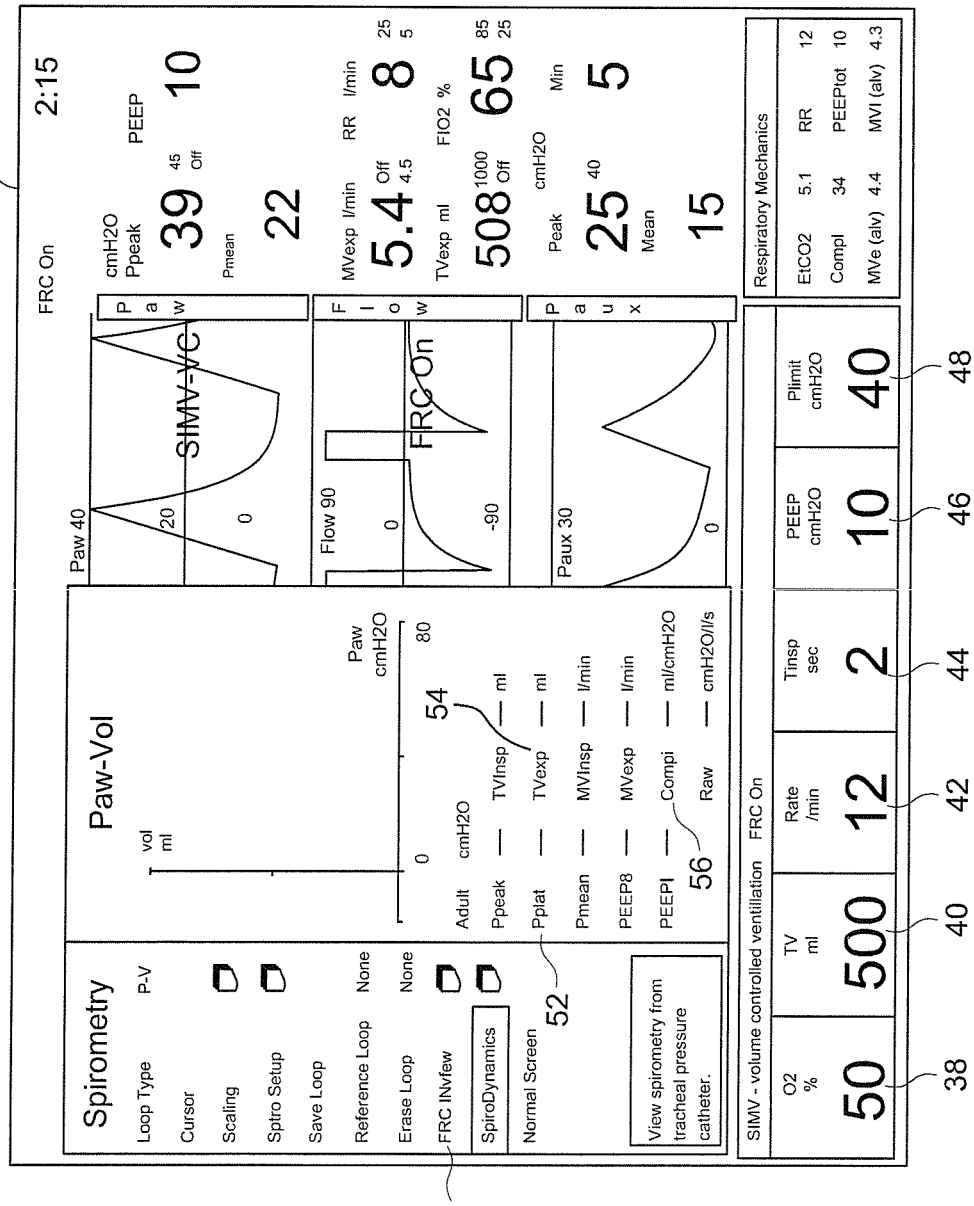
FIG. 2 is an embodiment of a graphical user interface for a ventilator system.

FIG. 2 depicts an embodiment of a graphical user interface (GUI) 36 such as may be presented by a graphical display 34 (FIG. 1). The GUI 36 is presented as an example of such a GUI that may be used in connection with the ventilator system 10 and the methods disclosed herein. The GUI 36 displays set or measured values associated with the respiratory therapy provided to the patient by the mechanical ventilator. The set values, displayed exemplarily for the provision of volume controlled ventilation, include oxygen percentage 38, tidal volume 40, respiratory rate 42, inspiratory interval 44, PEEP 46, and pressure limit 48. The GUI further displays measured values for Functional Residual Capacity (FRC) 50, pressure plateau (Pplat) 52, expiratory tidal volume 54, compliance (Cstat) 56. Therefore, it is to be noted that embodiments of the methods disclosed herein may be performed using measurements and settings obtained directly from the mechanical ventilator 12 and presented on the GUI 36.

Figure 3:
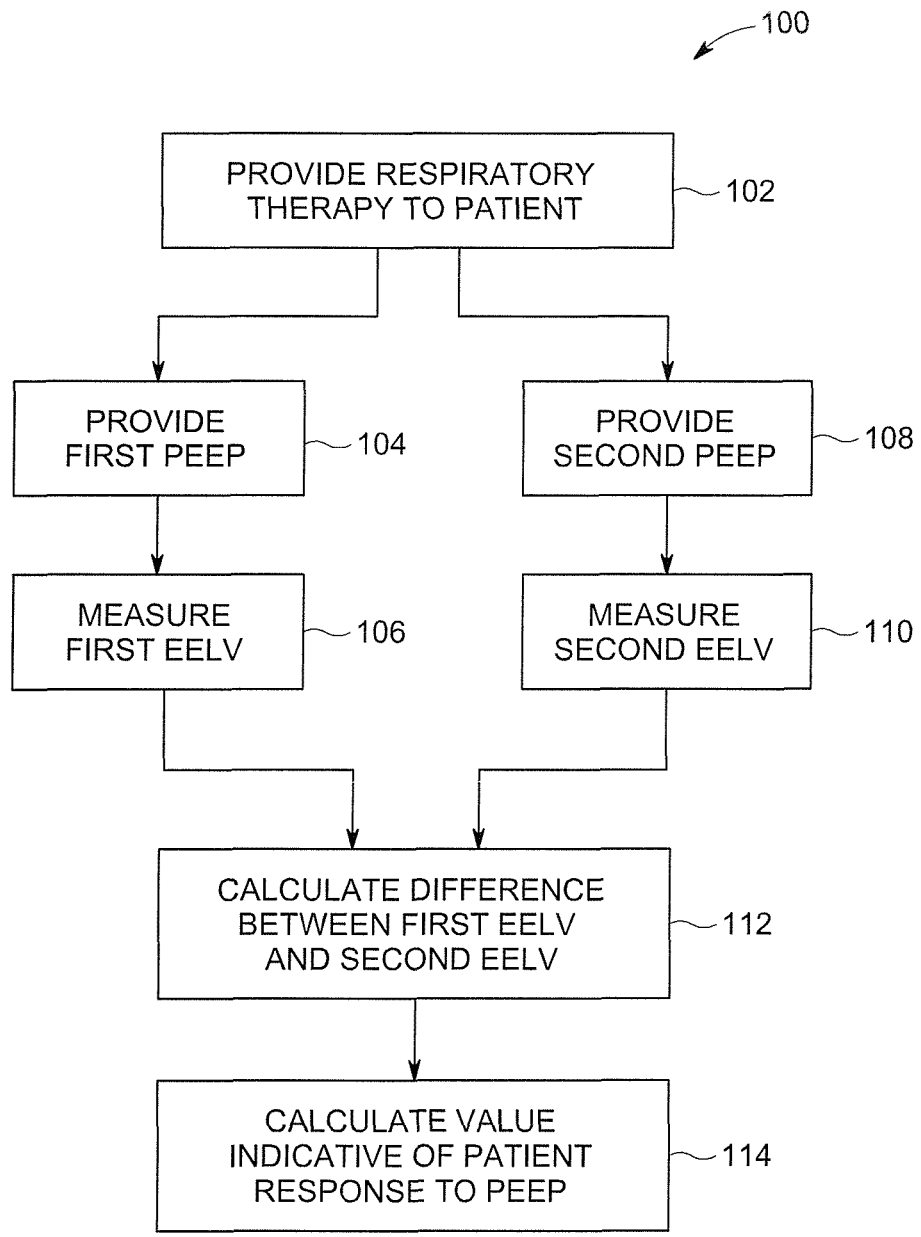
FIG. 3 is a flow chart depicting an embodiment of a method for automatedly evaluating a patient for PEEP therapy.

FIG. 3 is a flow chart depicting an embodiment of a method 100 of automatedly evaluating a patient for PEEP therapy.

At 102, respiratory therapy is provided to the patient, such as with the ventilator system 10 depicted in FIG. 1.

At 104, the respiratory therapy is provided to the patient at a first PEEP. In an embodiment, the first PEEP is a low Peep, which exemplarily provided to the patient at 5 cm $H_2O$. It is alternatively understood that the first PEEP could be zero PEEP (ZEEP). In that alternative embodiment, the evaluation would measure the effectiveness of the application of a PEEP pressure to a patient that currently does not receive PEEP therapy.

Next, a first EELV is measured by the gas monitoring sensor. In an embodiment, the gas monitoring sensor may be a volumetric sensor. Alternatively, the gas monitoring sensor may be a flow sensor, a pressure sensor, a concentration sensor, or a combination thereof.

The first EELV may be measured in a variety of ways. Any of which techniques are considered within the scope of the present disclosure, as were others that would be recognized by one of ordinary skill. Examples of techniques used to measure first EELV may be body pleythysmography, helium dilution, or inert gas wash-out techniques.

If the first PEEP provided at 104 is ZEEP, then the first EELV measured at 106 will be the patient's FRC. In some embodiments, it may be desired to obtain FRC while minimizing the time that the patient's respiratory therapy is lowered to ZEEP. Often, the techniques identified above for measuring EELV require maintaining the patient at ZEEP for 120-180 seconds. An attending clinician may not desire to have the patient go without PEEP therapy for this length of time.

An alternative technique for the measurement of FRC has been developed to limit the patient's exposure without PEEP therapy. In this alternative technique, EELV at a low PEEP is measured. A single 12 second long expiration maneuver is performed to drop the patient from the low PEEP to ZEEP. The volume of expired air during this maneuver is measured and subtracted from the measured EELV to obtain FRC. After the expiration maneuver, PEEP therapy is resumed for the patient.

At 108, a second PEEP level is provided to the patient. In an embodiment, the second PEEP is a high PEEP, which exemplarily may be 15 cm $H_2O$. Alternatively, if the first PEEP at 104 is ZEEP, then the second PEEP 108 may be a low PEEP, exemplarily 5 cm $H_2O$, or may be the high PEEP. It is further understood that the first PEEP and the second PEEP may be provided to the patient in any order.

After the second PEEP is provided at 108, a second EELV is measured at 110. The second EELV may be measured in any of the manners described above with respect to the measurement of the first EELV.

At 112, a difference between the first EELV and the second EELV is calculated. The difference between the first EELV and the second EELV calculated at 112 represent the total change in expiratory lung volume ($\Delta$EELV) that is attributable to a change in PEEP therapy. This change may result from an increase in PEEP from ZEEP to the low PEEP or to the high PEEP. Alternatively, the change may be attributable to an increase in PEEP from the low PEEP to the high PEEP. Finally, at step 114, the CPU 132 calculates a value that is indicative of the patient's response to PEEP therapy. The calculated value uses the difference between the first EELV and the second EELV calculated by the CPU at 112.

In one embodiment, the calculated value indicative of the patient's response to PEEP therapy is a recruitment index. The recruitment index is calculated as a ratio of the difference between the first EELV and the second EELV ($\Delta$EELV) and a patient lung volume. In one specific embodiment, the recruitment index is the ratio of the change between the first EELV and the second EELV and the patient's FRC. This example is represented in the equation:

$$\text{RECRUITMENT INDEX} = \Delta\text{EELV}/\text{FRC}$$

In alternative embodiments, the recruitment index is a ratio between $\Delta$EELV and one of the first EELV or the second EELV.

The recruitment index may be presented on the GUI 36 as a percentage. An evaluation of the recruitment index can be used to differentiate between patients that are high recruiters and patients that are low recruiters. The recruitment index has been found to correlate with the percentage of the $\Delta$EELV associated with alveolar recruitment.

A predetermined threshold value can be established such as to distinguish the high recruiters, which are good candidates for PEEP therapy, from the low recruiters, which are poor candidates for PEEP therapy. Based upon initial research, such a predetermined threshold value may be a recruitment index of 73%, however, this is not intended to be limiting on the range within which the predetermined threshold value may fall, as it is understood that upon further research, additional ventilation conditions, or patient demographics, the predetermined threshold value may be revised and therefore is not restricted to any particular value range in the present disclosure.

In exemplary embodiments, the exemplary threshold of 73% has been found to have a sensitivity of 80, a specificity of 80%, a positive likelihood ratio of 4.0 and a negative likelihood ratio of 0.25.

In an alternative embodiment, the value indicative of patient response to PEEP calculated at 114 is an alveolar recruitment volume. The alveolar recruitment volume may be calculated as the difference between $\Delta$EELV calculated at 112 and a calculated minimal predicted increase in lung volume (MPILV). The MPILV may be calculated by the CPU. The MPILV can be calculated as the product between the static compliance (Cstat) of the patient calculated at low PEEP and the difference between the first PEEP and the second PEEP ($\Delta$PEEP). MPILV may be represented with the equation:

$$\text{MPILV (mL)} = C\text{stat (mL/cm } H_2O) \times \Delta\text{PEEP (cm } H_2O)$$

Cstat can be calculated at low PEEP with the equation:

$$C\text{stat (ml/cm} H_2O) = \text{tidal volume (mL)}/(P\text{plat (cm}H_2O) - \text{low PEEP (cm}H_2O))$$

In the above equation, Pplat is the plateau pressure measured at low PEEP and the low PEEP may exemplarily be the first PEEP that is provided to the patient at 104.

The MPILV is an estimation of a minimal lung volume increase attributable to a change in PEEP. The MPILV is representative of the increase in EELV obtained through lung distention.

Returning to the calculation of alveolar recruitment volume, the difference between $\Delta$EELV and MPILV is therefore an estimate of the volume from $\Delta$EELV that is attributable to alveolar recruitment. Alveolar recruitment volume may be represented by the equation:

$$\text{Alveolar Recruitment} = \Delta\text{EELV (mL)} - \text{MPILV (mL)}$$

Since the MPILV is a component of $\Delta$EELV, the MPILV must be necessarily about equal to or less than $\Delta$EELV. Because $\Delta$EELV is calculated from measured values and MPILV is a calculated estimate, it is understood that when alveolar recruitment is minimal or non-existent, due to margins of error, the MPILV may be greater than $\Delta$EELV. In such embodiments, if the MPILV is 10 mL, or more, greater than $\Delta$EELV, the values should be remeasured and recalculated as this is indicative of errors in obtaining $\Delta$EELV or MPILV.

In most instances, however, $\Delta$EELV will be greater than MPILV as the $\Delta$EELV will have a distention component and a recruitment component. The alveolar recruitment volume, therefore, is an estimated volume of the recruitment component of the measured $\Delta$EELV.

A predetermined threshold value may be established for use in evaluating the estimated alveolar recruitment volume. In an embodiment, the predetermined threshold value may be established as a value between 100 mL and 200 mL. In a more specific embodiment, the predetermined threshold value may be set at 150 mL. An alveolar recruitment greater than the predetermined threshold value may result in a patient being evaluated as a good candidate for PEEP therapy with a high potential for EELV obtained by alveolar recruitment. An alveolar recruitment volume less than the predetermined threshold may be indicative of a patient that is a poor candidate for PEEP therapy as little EELV is likely to be gained through alveolar recruitment.

While the embodiment of the method 100 has been described herein with respect to FIG. 3, it is understood that alternative embodiments of the method may perform the steps identified herein in an alternative order or in connection with more or fewer steps than have been described herein.

Figure 4:
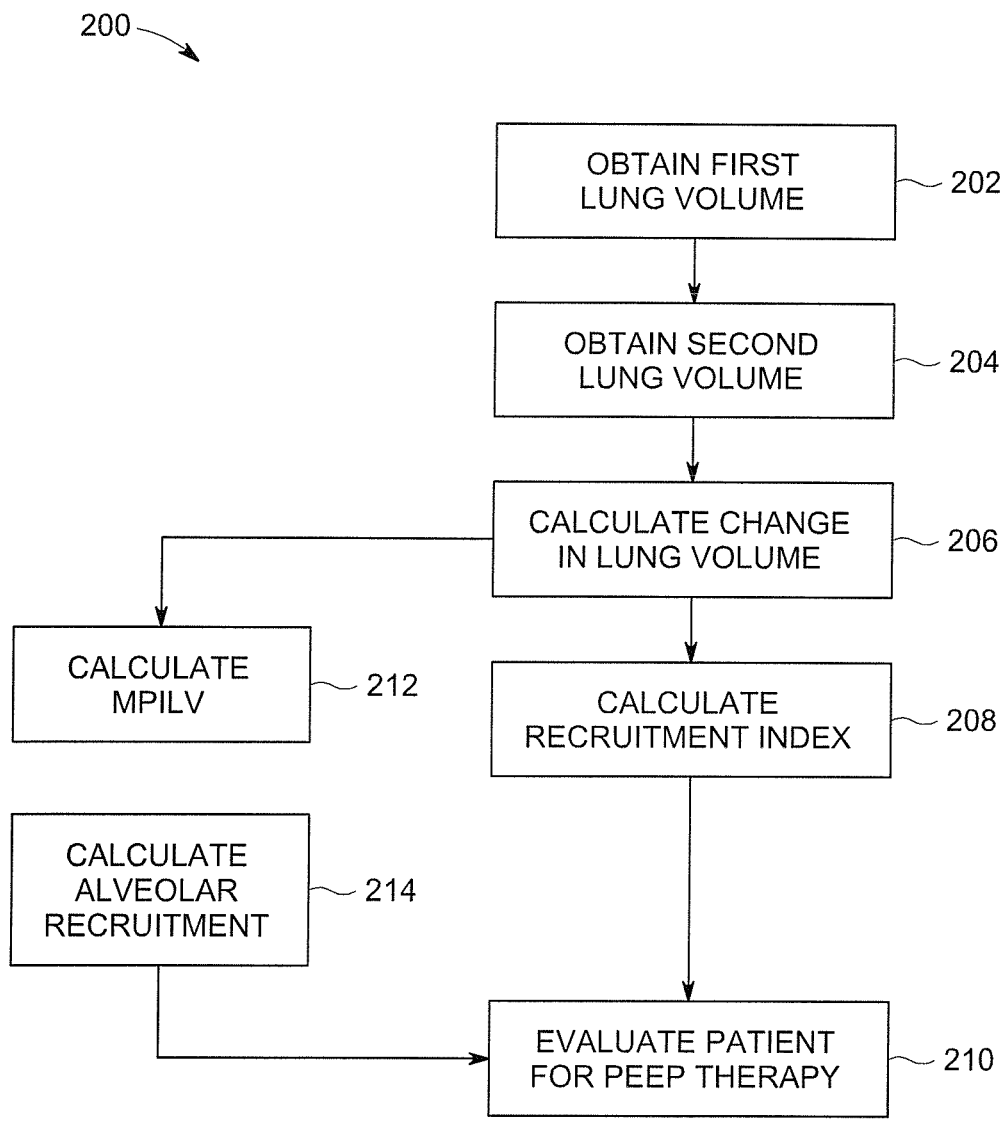
FIG. 4 is a flow chart depicting an embodiment of a computer implemented method for automatedly evaluating a patient for PEEP therapy.

FIG. 4 is a flow chart that depicts an alternative embodiment of a method 200 of evaluating a patient for PEEP therapy. Embodiments of the method 200 may be stored as computer readable code on a non-transitory computer readable medium. The execution of the computer readable code by a computer processor may cause the processor to perform the method 200.

At 202, a first lung volume is obtained. As noted above, the first lung volume may be an EELV. At 204, a second lung volume is obtained. The second lung volume may also be an EELV. It is understood that the first lung volume and the second lung volume are different lung volumes obtained from the same patient. The variation in the lung volumes are due to the application of two different levels of PEEP on a patient. If no PEEP is provided to the patient, then the lung volume is an FRC of the patient. Therefore, one of the first lung volume and second lung volume is a low EELV, which is generally obtained at a PEEP between zero and ten. The other of the first lung volume and the second lung volume is a high EELV, which is generally obtained at a PEEP greater than zero, and greater than the PEEP associated with the low EELV.

Next, at 206, the change in lung volume is calculated between the first lung volume and the second lung volume. Generally, the change in lung value is represented as a positive number, by subtracting the low EELV value from the high EELV value to arrive at a $\Delta$EELV value.

At 208, the recruitment index is calculated. As noted above with respect to method 100, the recruitment index is a ratio of the change in lung volume to another lung volume In one embodiment the recruitment index is the ratio of $\Delta$EELV to FRC. In alternative embodiments, the recruitment index may be the ratio of $\Delta$EELV to either of low EELV or high EELV.

At 210, the recruitment index calculated at 208 is used to evaluate the patient for PEEP therapy. As noted above, the recruitment index can differentiate a patient that will experience high alveolar recruitment from the introduction or increase of PEEP therapy versus those patients that will see little recruitment benefit from the increased pressure applied to the lungs.

Additional embodiments of the method 200 calculate MPILV at 212. MPILV is calculated in the manner described above with respect to the method 100. Once the MPILV is calculated, alveolar recruitment volume can be calculated at 214.

As noted above, the alveolar recruitment volume is an estimate of the volume of the change in lung volume from 206 that is attributable to alveolar recruitment. In alternative embodiments, the evaluation of the patient for PEEP therapy at 210 may further include the alveolar recruitment calculated at 214. The evaluation of the patient for PEEP therapy based upon two measurements of recruitment may therefore provide a more robust analysis of the potential effectiveness of PEEP therapy for the patient.

Figure 5:
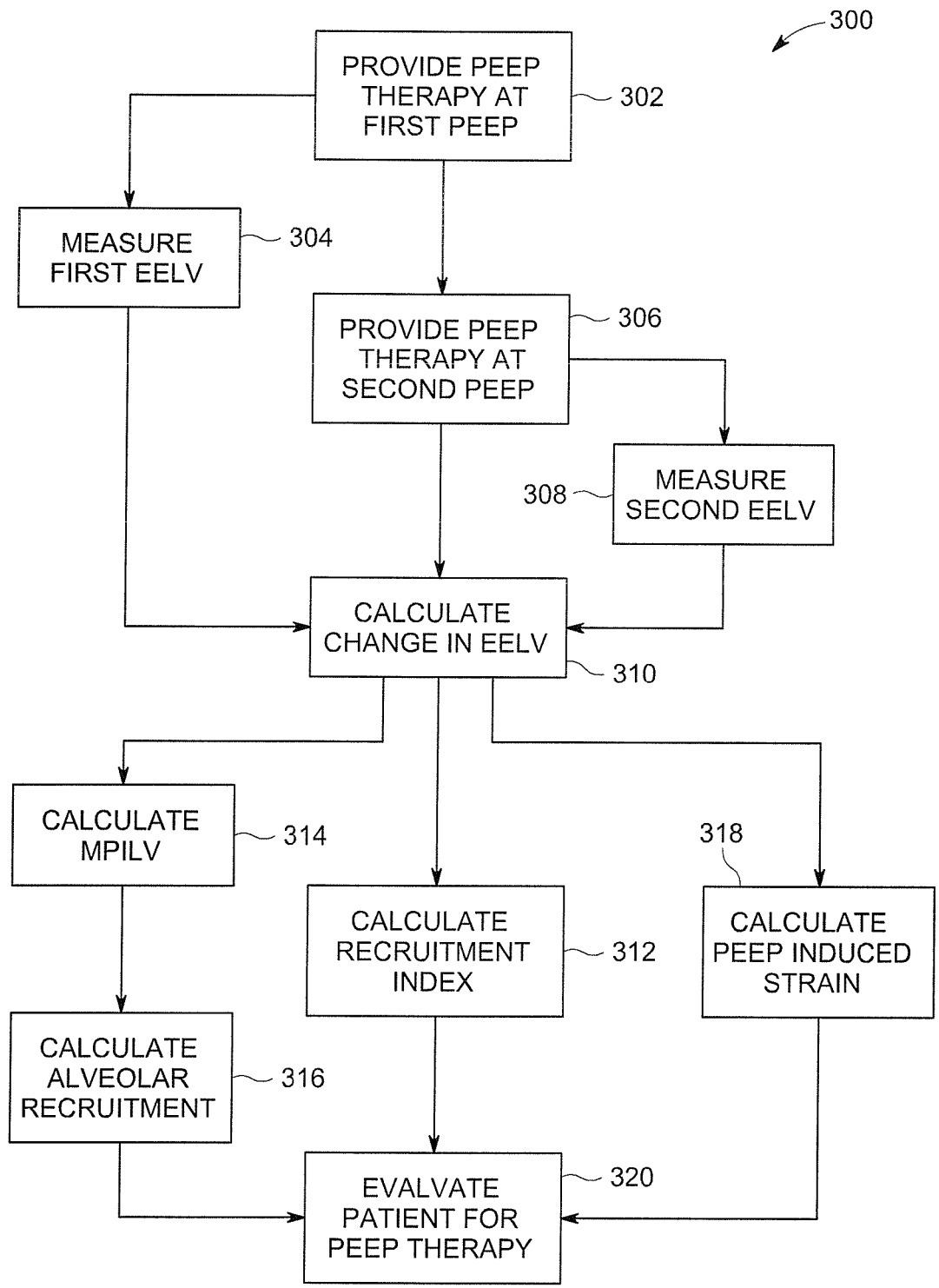
FIG. 5 is a flow chart depicting an alternative embodiment of a method of automatedly evaluating a patient for PEEP therapy.

FIG. 5 is flow chart that depicts the steps of an embodiment of an alternative method 300 of automatedly evaluating a patient for PEEP therapy.

At 302, PEEP therapy is provided to the patient by a mechanical ventilator at a first PEEP. In non-limiting embodiments disclosed herein, the first PEEP is a low PEEP, exemplarily 5 cm $H_2O$. At 304, a first EELV is measured while the patient is ventilated at the first PEEP. As noted above, a variety of methods and techniques for calculating EELV are known or recognized by one of ordinary skill in the art, any of which may be used in embodiments of the method 300. In an alternative embodiment, the first PEEP is ZEEP and the first EELV is FRC.

Next, at 306, the patient is provided with PEEP therapy from the mechanical ventilator at a second PEEP. As a non-limiting example, the second PEEP is a high PEEP, exemplarily 15 cm $H_2O$. At 308, a second EELV is measured while the patient receives PEEP therapy at the second PEEP. In the alternative embodiment wherein the first PEEP is ZEEP, and the first EELV is FRC, the second PEEP may be a low PEEP or a high PEEP.

At 310, a change in lung volume ($\Delta$EELV) is calculated between the first EELV and the second EELV.

At 312, the $\Delta$EELV from 310 is used to calculate a recruitment index as the ratio of the calculated change in lung volume to a measured lung volume. In An embodiment, the recruitment index is a ratio of the $\Delta$EELV to the FRC. In this embodiment, the recruitment index is representative of the percentage increase in EELV obtained over FRC by the application of PEEP therapy. As noted above, this recruitment index has been found to be correlated with recruitment volume. In alternative embodiments, the recruitment index may be the ratio of the $\Delta$EELV to either the first EELV or the second EELV.

At 314, MPILV is calculated from the change in lung volume calculated at 310 and a calculated static compliance of the patient's lungs. The MPILV calculated at 214 is used to calculate the alveolar recruitment volume at 316. The alveolar recruitment volume is the difference between the change in the lung volume from 310 and the MPILV from 314. The alveolar recruitment volume calculated at 316 is an estimate of the change in lung volume that is attributable to alveolar recruitment by the application of PEEP.

At 318, PEEP induced strain is calculated. PEEP induced strain is a measure of the strain on the lungs that is induced by the added pressure from PEEP therapy. The PEEP induced strain identifies a portion of the change in lung volume from 310 that is attributable to the distention of the lungs. PEEP induced strain may be calculated with the equation:

$$\text{strain} = (\Delta\text{EELV (mL)} - \text{alveolar recruitment (mL)}) / \text{FRC (mL)}$$

Alternatively, since $\Delta$EELV−alveolar recruitment=MPILV, PEEP induced strain may be alternatively calculated by the equation:

$$\text{strain} = \text{MPILV}/\text{FRC}$$

It is to be understood that alternative embodiments may calculate PEEP induced strain using the low EELV or the high EELV.

Finally, at 320 a patient is automatically evaluated for PEEP therapy. The evaluation of the patient for PEEP therapy at 320 may include some or all of the recruitment index calculated at 312, the alveolar recruitment volume calculated at 316, and the PEEP induced strain calculated at 318. While the use of one of the above noted recruitment index, alveolar recruitment volume, and PEEP induced strain may provide the required evaluation of the patient for PEEP therapy, in some embodiments, a combination of two or more of the above noted values may provide a more robust evaluation. The evaluation of the patient for PEEP therapy identifies the patient as a good candidate for PEEP therapy or a poor candidate for PEEP therapy. A good candidate for PEEP therapy is a candidate that is expected to gain significant amount of EELV due to the PEEP, with a significant portion of that new lung volume being attributable to alveolar recruitment, and that such benefits are provided with minimized PEEP induced strain. To the contrary, a poor candidate for PEEP therapy is estimated to gain limited additional EELV, much of which is attributable to lung distention, resulting in a high level of PEEP induced strain.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of automatedly evaluating a patient for positive end expiratory pressure (PEEP) therapy, the method comprising:
   providing respiratory assistance to the patient with a mechanical ventilator; providing PEEP therapy at a first PEEP to the patient with the mechanical ventilator;
   measuring a first end expiratory lung volume (EELV) of the patient at the first PEEP with a gas monitoring module associated with the mechanical ventilator;
   providing PEEP therapy at a second PEEP to the patient with the mechanical ventilator;
   measuring a second EELV of the patient at the second PEEP with the gas monitoring module;
   calculating a difference between the first EELV and the second EELV with a processor of the mechanical ventilator;
   calculating, with the processor, a recruitment index indicative of the patient's response to PEEP therapy wherein the recruitment index is a ratio of the difference between the first EELV and the second EELV to a measured lung volume of the patient;
   determining, based upon the calculated recruitment index, whether lung distention or alveolar recruitment make up a greater portion of the difference between the first EELV and the second EELV; and
   controlling the respiratory assistance provided to the patient with the mechanical ventilator based upon the determination.

2. The method of claim 1, wherein the measured lung volume is selected from the first EELV, the second EELV and a functional residual capacity (FRC) of the patient.

3. The method of claim 1, further comprising:
   comparing the recruitment index to a predetermined threshold representative of patient response to PEEP therapy;
   wherein if the recruitment index is greater than the predetermined threshold, alveolar recruitment makes up a greater portion of the difference between the first EELV and the second EELV; and
   wherein if the recruitment index is less than the predetermined threshold, lung distention makes up a greater portion of the difference between the first EELV and the second EELV.

4. The method of claim 3, wherein the predetermined threshold is between 0.70 and 0.80.

5. The method of claim 1, further comprising
   producing an evaluation indicative if the patient is a good candidate to receive PEEP therapy or a poor candidate to receive PEEP therapy;
   wherein the patient is a good candidate for PEEP therapy if a greater portion of the difference between the first EELV and the second EELV is due to alveolar recruitment; and
   wherein the patient is a poor candidate for PEEP therapy if a greater portion of the difference between the first EELV and the second EELV is due to lung distention.

6. A non-transient computer readable medium comprising computer readable code that upon execution by a processor, causes the processor to:
   obtain a first end expiratory lung volume (EELV) at a first positive end expiratory pressure (PEEP); obtain a second EELV at a second PEEP;
   calculate a change in lung volume between the first EELV and the second EELV;
   calculate a recruitment index by dividing the change in lung volume by a measured third EELV:
   control respiratory assistance provided to the patient with the mechanical ventilator to continue PEEP therapy or cancel PEEP therapy based upon the recruitment index, compare the recruitment index to a predetermined threshold value to determine if a greater portion of the change in lung volume is attributed to alveolar recruitment or lung distention and control the respiratory assistance provided to the patient; and
   wherein a greater portion of the change in lung volume is attributed to alveolar recruitment and PEEP therapy is continued if the recruitment index is greater than the predetermined threshold and a greater portion of the change in lung volume is attributed to lung distention and PEEP therapy is cancelled if the recruitment index is less than the predetermined threshold and
   controlling the respiratory assistance provided to the patient with the mechanical ventilator based upon the determination.

7. The computer readable medium of claim 6 which further causes the processor to:
   calculate a minimal predicted increase in lung volume (MPILV); and
   calculate an alveolar recruitment volume as the difference between the change in lung volume and the MPILV;
   wherein the processor further controls the respiratory assistance provided to the patient to continue or cancel PEEP therapy based upon the alveolar recruitment volume.

8. The computer readable medium of claim 6, wherein the third EELV is a functional residual capacity (FRC).

9. A method of automatedly evaluating a patient for positive end expiratory pressure (PEEP) therapy, the method comprising:
   providing PEEP therapy at a first PEEP to the patient with a mechanical ventilator;
   measuring a first end expiratory lung volume (EELV) of the patient at the first PEEP with a sensor connected to the mechanical ventilator, providing PEEP therapy at a second PEEP to the patient with the mechanical ventilator;

measuring a second EELV of the patient at the second PEEP with the sensor;

calculating a change in volume between the first EELV and the second EELV with a processor of the mechanical ventilator;

calculating, with the processor, a recruitment index as a ratio of the change in volume to a lung volume;

calculating a minimal predicted increase in lung volume (MPILV) by multiplying a static compliance of the patient at the first PEEP by a difference between the first PEEP and the second PEEP;

calculating a PEEP induced strain by dividing the MPILV by the second EELV; and determining, based upon the recruitment index, alveolar recruitment volume, and the PEEP induced strain, whether lung distention or alveolar recruitment make up a greater portion of the change in volume between the first EELV and the second EELV;

identifying the patient as a good candidate for PEEP therapy if alveolar recruitment makes up a greater portion of the change in volume and identifying the patient as a poor candidate for PEEP therapy if lung distention makes up a greater portion of the change in volume; and controlling the PEEP therapy provided to the patient with the mechanical ventilator based upon the identification of the patient as a good candidate for PEEP therapy or a poor candidate for PEEP therapy; and controlling the respiratory assistance provided to the patient with the mechanical ventilator based upon the determination.

10. The method of claim 9, further comprising:

measuring a functional residual capacity (FRC) with the sensor;

wherein the recruitment index is a ratio of the change in volume to the FRC.

11. The method of claim 9, wherein the recruitment index is a ratio of the change in volume to either the first EELV or the second EELV.

12. A method of automatedly evaluating a patient for positive end expiratory pressure (PEEP) therapy, the method comprising:

providing respiratory assistance to the patient with a mechanical ventilator;

providing PEEP therapy at a first PEEP to the patient with the mechanical ventilator;

measuring a first end expiratory lung volume (EELV) of the patient at the first PEEP with a gas monitoring module associated with the mechanical ventilator;

providing PEEP therapy at a second PEEP to the patient with the mechanical ventilator;

measuring a second EELV of the patient at the second PEEP with the gas monitoring module;

calculating a difference between the first EELV and the second EELV with a processor of the mechanical ventilator;

calculating a minimal predicted increase in lung volume (MPILV);

calculating, with the processor, a value indicative of the patient's response to PEEP therapy, wherein the value is an alveolar recruitment volume calculated as a difference between the first and second EELV and the MPILV; and determining, based upon the alveolar recruitment volume, whether lung distention or alveolar recruitment make up a greater portion of the difference between the first and second EELV;

producing an evaluation indicative if the patient is a good candidate to receive PEEP therapy if alveolar recruitment makes up a greater portion of the difference between the first and second EELV or the patient is a poor candidate to receive PEEP therapy if lung distention makes up a greater portion of the difference between the first and second EELV; and controlling the respiratory assistance provided to the patient with the mechanical ventilator based upon the determination.

13. The method of claim 12, wherein the MPILV is calculated by the processor as the product of a static lung compliance of the patient and a difference between the first PEEP and the second PEEP.

14. The method of claim 13, further comprising:

comparing the alveolar recruitment volume to a predetermined threshold representative of a patient response to PEEP therapy;

wherein if the alveolar recruitment volume is greater than the predetermined threshold, the processor evaluates the patient as a good candidate for PEEP therapy; and wherein if the alveolar recruitment volume is less than the predetermined threshold, the processor evaluates the patient as a poor candidate for PEEP therapy.

15. The method of claim 14, wherein the predetermined threshold is between 100 mL and 200 mL.

16. The method of claim 15, wherein a good candidate for PEEP therapy is a patient that is likely to gain lung volume by alveolar recruitment when PEEP is applied, and a poor candidate for PEEP therapy is likely to gain lung volume by lung distention when PEEP is applied.

* * * * *